United States Patent [19]

Kinsel

[11] Patent Number: 5,749,726
[45] Date of Patent: May 12, 1998

[54] DISPOSABLE POINT OF USE FILTRATION ELEMENT FOR PURIFYING AIR AND WATER SUPPLIES TO DENTAL HANDPIECES

[75] Inventor: David I. Kinsel, Sylvania, Ohio

[73] Assignee: Gelman Sciences, Ann Arbor, Mich.

[21] Appl. No.: 397,396

[22] Filed: Mar. 2, 1995

[51] Int. Cl.$^6$ .............................. A61G 17/02; A61C 1/08
[52] U.S. Cl. ................................................ 433/80; 433/126
[58] Field of Search .......................... 433/80, 81, 84, 433/85, 88, 126; 210/321.64, 321.72, 321.75, 321.84, 251

[56] References Cited

U.S. PATENT DOCUMENTS

| | | | |
|---|---|---|---|
| 4,629,425 | 12/1986 | Detsch | 433/80 X |
| 4,869,668 | 9/1989 | Seney | 433/85 |
| 4,950,159 | 8/1990 | Hansen | 433/80 |
| 5,204,004 | 4/1993 | Johnston et al. | 210/651 |
| 5,308,483 | 5/1994 | Sklar et al. | 210/321.75 X |
| 5,405,528 | 4/1995 | Selbie et al. | 210/371.72 X |

OTHER PUBLICATIONS

"A Method of Decontamination of Ultrasonic Scalers and High Speed Handpieces", M.B. Dayoub, et al. *J. Periodontol.*, May, 1978, pp. 261–265.

*Primary Examiner*—Robert P. Swiatek
*Assistant Examiner*—Yvonne R. Abbott
*Attorney, Agent, or Firm*—Brooks & Kushman P.C.

[57] ABSTRACT

A point of use microfiltration device suitable for filtering the cooling water and cooling air supplies to a turbine driven dental handset is a multicompartmental device containing microporous filtration membranes effective to remove particulate matter, particularly microbes, thus protecting the patient from the risk of infection. The device contains passages providing for unrestricted turbine supply and return air, and may be provided with a light path suitable for use with fiber optic light supplies. The device is advantageously constructed to mate with standard multilumen and handpiece end fittings, and may be disposed of after a single use.

16 Claims, 6 Drawing Sheets

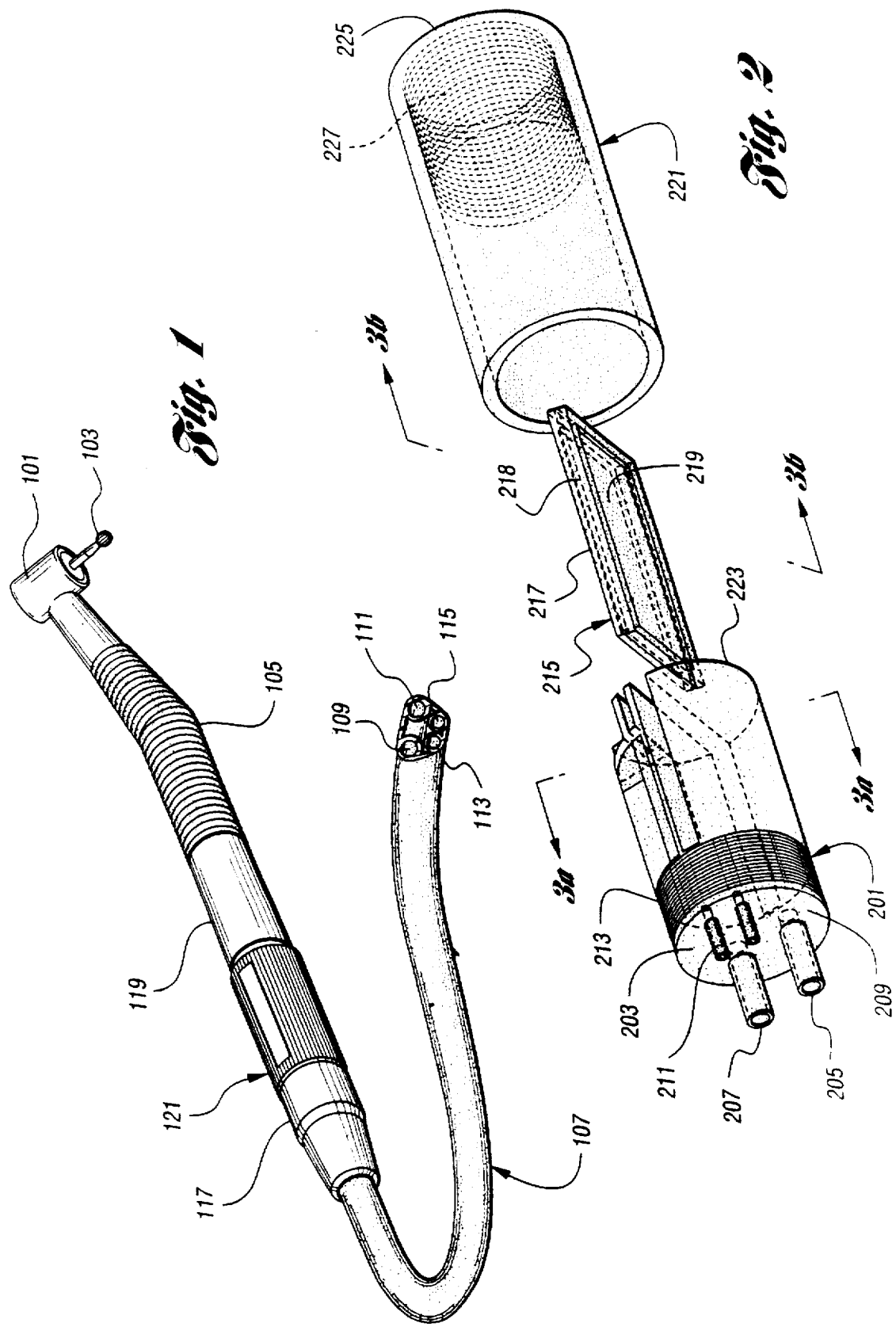

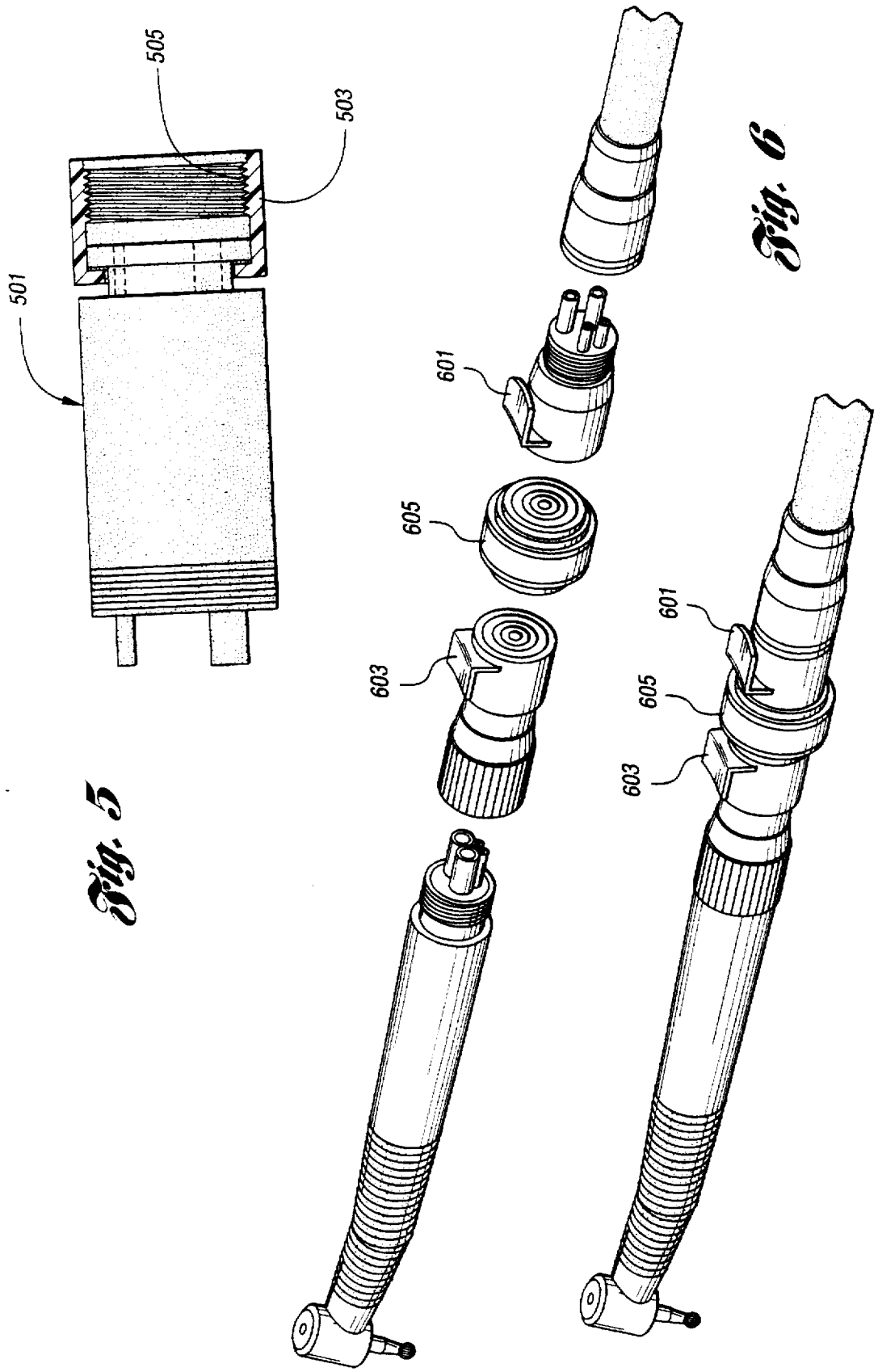

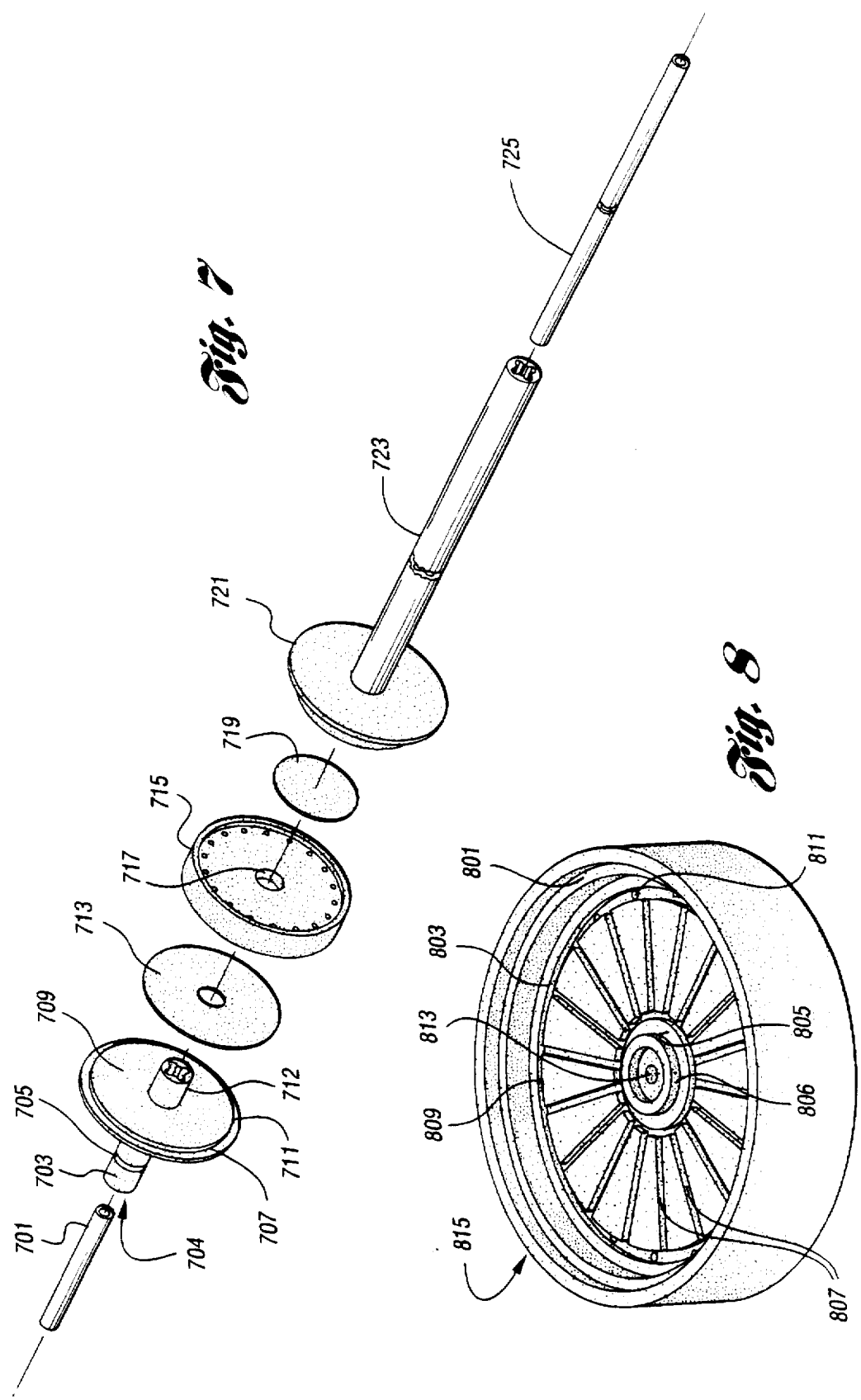

5,749,726

DISPOSABLE POINT OF USE FILTRATION ELEMENT FOR PURIFYING AIR AND WATER SUPPLIES TO DENTAL HANDPIECES

TECHNICAL FIELD

The present invention pertains to a filtration element suitable for purifying the air and water supplies to turbine driven dental handpieces. More particularly, the present invention pertains to a disposable filter element capable of removing microorganisms and other contaminants from both the air and water supplies to the handpiece. The filtration element contains both hydrophobic and hydrophilic microporous membranes and is small enough to avoid interference with the work of the handpiece.

Modern dental practices, whether associated with restoration or prophylaxis, involve both the influx of water and air into the patient's oral cavity as well as the ejection or removal of saliva and debris. While in prior years little attention was devoted to ensuring biologically pure water and air supplies, the reverse is now true, particularly in view of concerns with transmission of infectious diseases such as hepatitis and HIV, as well as concerns relative to previously unrecognized general infection (sepsis) which may result when infectious agents encounter cut or abraded oral tissue.

Although heightened hygiene in dental work has fostered the wide-spread use of rubber gloves, face masks, and high temperature sterilization of dental implements, the air and water supplies, both of which are prime conduits for infectious agents, have received attention. Compressed air supplies, for example, have been connected to traditional filter elements containing fibrous material, for example cotton or fiber glass. While such filters are effective to remove oil mist from compressors, dust, and other particulate matter of large dimension, they are of little effectiveness with regard to microbes such as bacteria and viruses. Moreover, the microbes which are removed may reproduce in the filter elements themselves, ultimately contributing to microbe contaminated air.

Water supplies have also been traditionally filtered, either by fibrous or wound filters or by beds of activated carbon, zeolites, alumina, etc. Such beds are notorious for harboring microbes, however, and thus such filters, while being effective to remove major particulates, and, in the case of activated carbon, organic contaminants, have only marginal effectiveness with respect to microorganisms, with even this marginal effectiveness being of short duration.

In U.S. Pat. No. 4,950,159 is disclosed a filter element for a dental syringe in which a longitudinal filter element divided into two compartments filters the water and air supplies just prior to dispersal from the syringe. However, the filtration elements are activated charcoal for the water supply and cotton fleece for the air supply. Neither of these filtration elements is well suited to eliminate microbes from the respective supplies. Moreover, the device allows contaminated air and water to be backflushed into the supply systems should a reduction in pressure occur, or even by remaining at static pressure for extended periods. The device is also not suited for turbine-driven handpieces (drills) where multiple air connections must be made by multilumen supply tubes. Moreover, the device is relatively expensive, currently between 20 and 30 dollars, and thus cannot be routinely discarded and replaced.

U.S. Pat. No. 5,204,004 discloses a filtration element for the water supply to a dental syringe, employing a microporous membrane. Unfortunately, the air supply is left unfiltered. As with the case of the device disclosed in the '159 patent, the element is not suitable for turbine-driven handpieces, nor is it readily adapted to the input fittings on many syringes in common use. Moreover, the device must be spliced into the supply tubing. Splicing more than one device into a multilumen supply is impractical as well as unaesthetic.

The most commonly used drilling or abrading tools in the modern dentist's office are air turbinedriven medium and high speed handpieces. These handpieces contain an air-driven turbine operating with pressurized, relatively high volume air. As the turbine itself is sealed, little risk of contamination is present even when the air supply to the turbine is not completely sterile. The modern handpieces operate at such higher speeds than those of prior eras that considerable heat may build up both at the burr itself and also at the teeth being drilled or shaped. To eliminate this heat build-up, cooling jets of air, water, or air/water mist are applied to the locus of the rotating burr. Unlike the sealed turbine air supply, the air and water used to cool the burr will come in contact with the patient's oral cavity, and if not free of microorganisms, may cause infection, particularly if the gums or mouth lining is inflamed, abraded, or cut.

As indicated previously, attempts to filter air and water supplies downstream from the chair have been largely ineffectual except with regard to removing major particulates and in some cases, organic contaminants. Insertion of water filters near the handpiece interfere with the attachment of the handpiece to the standard supply lines, while positioning a filter further away would involve a multiplicity of filters and adapters the installation and/or changing of which would be cumbersome and time-consuming. Furthermore, some modern handpieces come equipped with fiber optic light sources which interfere with filter placement.

SUMMARY OF THE INVENTION

It is an object of the present invention to provide a low cost, disposable microfiltration unit effective to remove particulate matter, particularly microbes such as bacteria, fungi, yeasts, and molds, from both the air and water cooling supplies directed to a turbine-driven handpiece.

These and other objects were achieved by a device which comprises a multi-compartmental filter of small physical size which may be connected between the handpiece and the standard air and water multilumen supply tube using standard connections, without interfering with the ease with which the handpiece may be maneuvered, and without defeating the ability to provide fiber optic lighting, when present. Not only does the subject filter device provide efficient filtering, but moreover, the design prevents backwashing of debris and microbial contamination from the patient into the supply lumen.

BRIEF DESCRIPTION OF THE DRAWINGS

FIG. 1 illustrates a typical turbine-driven handpiece and supply lumen with one embodiment of a filtration device of the subject invention inserted between the standard lumen connector and the handpiece;

FIG. 2 is an exploded view of one embodiment of the subject filtration device;

FIG. 5 illustrates a rotatable threaded collar for mounting on the outlet end of a multicompartmental filter device;

FIG. 6 illustrates a further embodiment of a disk-shaped multicompartmental filter device with durable connecting adapters and an assembled multilumen/filter/handpiece using these devices;

FIG. 7 is an exploded view of the central cooling air and cooling water filtration portions of a multicompartmental filter;

FIG. 8 is a view of the support grid of FIG. 7;

DESCRIPTION OF THE PREFERRED EMBODIMENTS

Figure 3A:
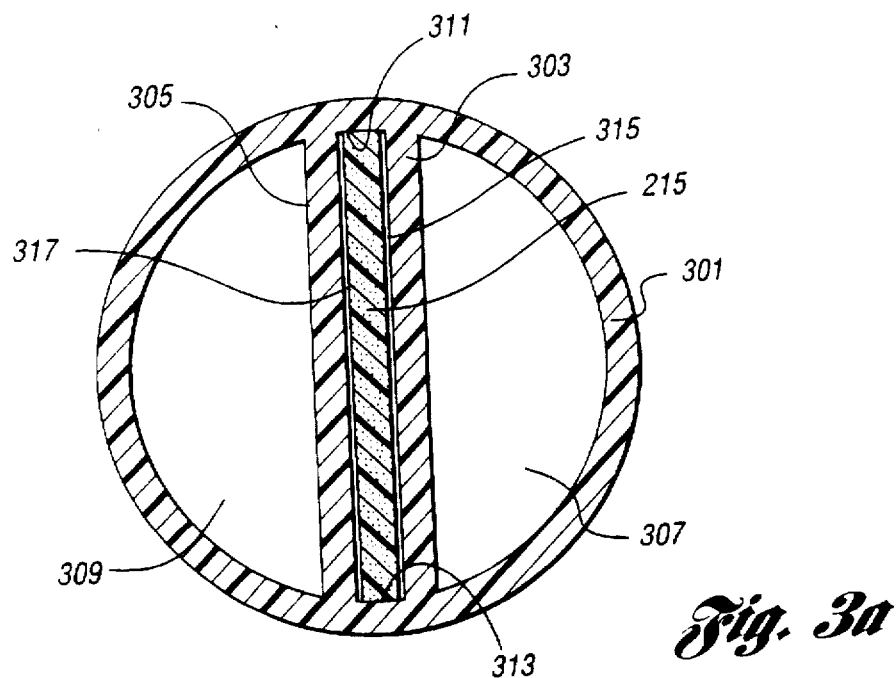
FIG. 3a is a cross-sectional view of the cylindrical inlet housing of FIG. 2 across its midlength.

The subject multicompartmental filter is a substantially cylindrical filter containing large cross-sectional area passageways for turbine supply and return air and relatively high surface area microporous filtration membranes adapted to filter the cooling air and cooling water supplies to remove all particulates, most especially microorganisms, having a predetermined minimum size, preferably about 1 µm, more preferably less than 0.45 µm. The preferred filtration device has, at one end, male fittings, extending away from the inlet end face, adapted to be inserted into a standard lumen female fitting, and at the other end, female fittings in the outlet end face adapted to receive a standard turbine-driven handpiece. The end having male fittings is threaded externally to secure it to the supply lumen, while the end having female fittings is fitted with an internally threaded collar or equivalent device to secure it to the handpiece. Alternatively, durable adapters may be provided to mate with the inlet and outlet faces of the multicompartmental filtration device and one or more standard multilumen and handpiece fittings.

The placement and working of the device may now be explained with reference to the drawings. With reference to FIG. 1, the turbine-driven handpiece head is shown at 101 with driven burr 103. The shaft 105 of the device contains passageways supplying high volume air to drive the turbine located in head 101 and a return passage for the driving air as well. Also located in shaft 105 are cooling air and cooling water lines.

The supply lumen 107 contains high volume air supply passage 109 and return air passage 111 as well as cooling air supply 115 and cooling water supply 113. As can be seen, the cross-section of supply lumen provides for these multiple passages in a standard configuration, and is terminated by sleeve 117. Sleeve 117 contains internal female connections which would normally mate with the male fittings in sleeve 119 of the handpiece. Sleeve 117 is threaded internally and is rotatable, while sleeve 119 is threaded at its end externally and is generally non-rotatable.

In FIG. 1, located between sleeve 117 of the supply lumen and sleeve 119 of the handpiece, is disposable filter element 121. As can be seen, the filter element 121 attaches to the supply lumen fittings and handpiece fittings in the same manner as would the handpiece to the supply lumen. Moreover, the filter element is small and unobtrusive, offering no impediment to normal handset usage.

In FIG. 2, an exploded view of one embodiment of the subject invention is illustrated. At 201 is an inlet housing having extending from the inlet face 203, male fittings 207 (turbine air supply), 205 (turbine air return) 211 (cooling water supply) and 209 (cooling air supply). At 213, the inlet housing is externally threaded to mate with the internally threaded sleeve of the supply lumen as illustrated in FIG. 1. The inlet housing, in this embodiment, contains two large cross-section compartments to provide a flow path for the turbine supply and return air, and two further compartments defining cooling air and cooling water chambers to receive unfiltered cooling air and cooling water from the lumen.

More specifically, the aforementioned compartments comprise a first compartment in communication with the turbine air supply passage in the inlet end and the turbine air supply passage in the outlet end. A second compartment is in communication with the turbine air return passage in the inlet end and the turbine air return passage in the outlet end. A third compartment is in communication with the cooling air inlet passage and the cooling air outlet passage, this third compartment containing a microporous air filtration membrane positioned such that all cooling air entering the device through the cooling air inlet passage must pass through the microporous air filtration membrane before exiting the device through the cooling air outlet passage. A fourth compartment is in communication with the cooling water inlet passage and the cooling water outlet passage, the fourth compartment containing a microporous water filtration membrane positioned such that all cooling water entering the device through the cooling water inlet passage must pass through the microporous water filtration membrane before exiting the device through the cooling water outlet passage.

The combined air and water filtration device is shown at 215. This device contains a microporous air filtration membrane 217 on one side and a microporous water filtration membrane 219 on the other, and is internally partitioned so as to maintain the cooling air and cooling water supplies completely separate. The surfaces of the device against which the filtration membranes are directed by fluid pressure are preferably ribbed so as to provide an adequate flow path for the fluid to be filtered and provide support for the membrane. Filtration is from the outside of filtration device 215 to the volume defined by the spaces between the ribs and the interior membrane 218. The filtration device slides into a slot in inlet housing 201 where it may be secured by solvent or adhesive bonding or other equivalent means.

At 221 is illustrated an outlet housing having an internal diameter adapted to slide over the inlet housing 201. The outlet housing may be secured by solvent or adhesive bonding within the annular space between the inlet and outlet housing cylinders, or the inlet housing end 223 may be bonded to a step in the bore of outlet housing 221. The outlet face 225 of outlet housing 221 contains bores comprising female fittings adapted to receive the corresponding male fittings of the turbine-driven handpiece. The end of outlet housing 221 is internally threaded at 227 to receive an internally threaded collar for mating the outlet of the device with the externally threaded handpiece. In a preferred embodiment, the housing carries a flange at its outlet end receiving a rotatable, internally threaded collar.

FIG. 3a is a view of cross-section A—A of FIG. 2. At 301 is the outside wall of the inlet housing while at 303 and 305 are two ribs which provide stiffening for the housing as well as defining compartments 307 and 309 through which high volume turbine supply and return air may travel unobstructed. Between ribs 303 and 305 is located the filter device shown as 215 in FIG. 2. The filter device is sealed to the housing at 311 and 313, by solvent bonding, for example. The interstices 315 and 317 communicate with the cooling water inlet and cooling air inlet fittings, respectively, to form low volume, high surface area filtration chambers.

Figure 3B:
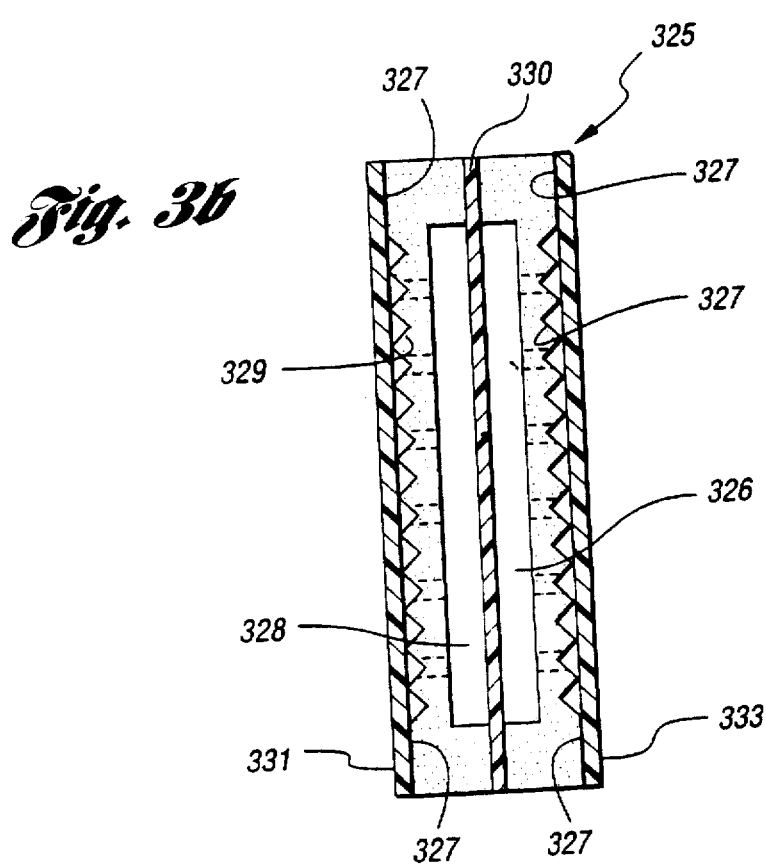
FIG. 3b is a cross-sectional view of the planar filter partition of FIG. 2 across its midsection perpendicular to the plane of the partition.

A view of cross-section B—B filtration device 215 of FIG. 2 is shown in FIG. 3b. The polymeric partition 325 contains on each of its filtration surfaces, grids 324 and 329 to provide channels for fluid flow. Air filtration microporous membrane 331 and water filtration microporous membrane 333 are sealed to the partition 325 at sealing surfaces 327. Water or air in the low volume filtration chambers surrounding the device passes through the respective membrane and flows towards the internal chambers 326 and 328, these chambers connected to the respective outlet fittings by internal passages in the outlet housing or an optional end cap. At 330 is a separator to keep the air and water chambers separate. Other arrangements of the filtration device will readily suggest themselves to the skilled artisan.

Figure 4:
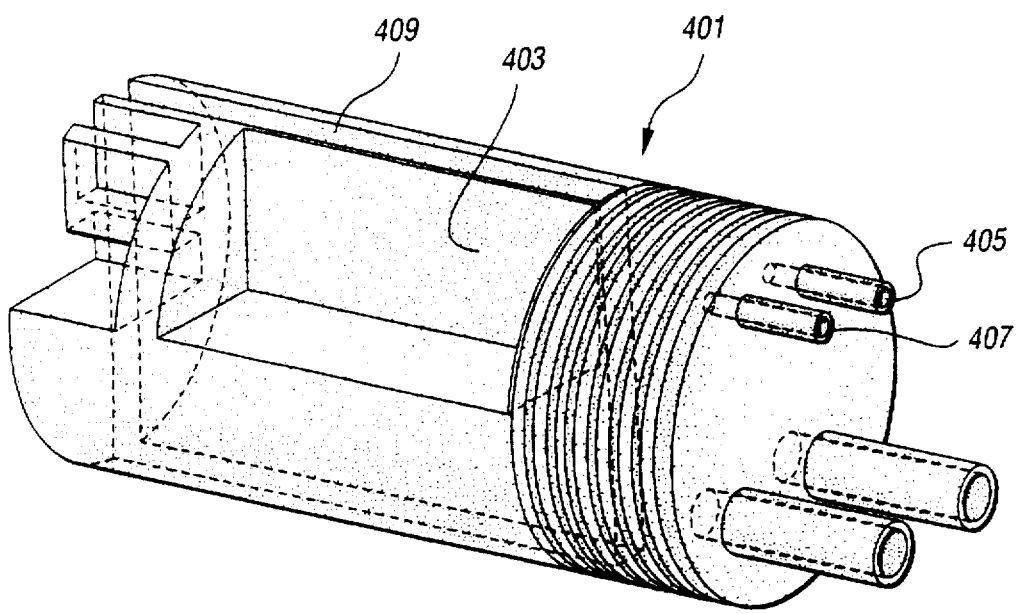
FIG. 4 is an enlarged view of an inlet housing as illustrated in FIG. 2.
Figure 4A:
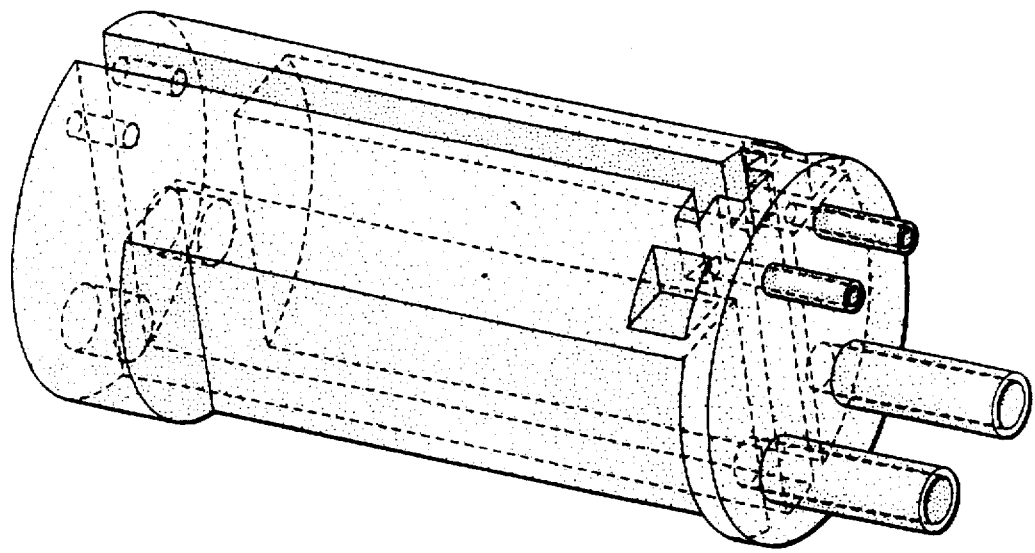
FIG. 4a is an embodiment of a combined inlet and outlet housing of a device similar to that of FIG. 2.

In FIG. 4 is shown an alternative embodiment of the inlet housing, where the housing body 401 is recessed by cutouts at 403 which stiffen the design and alleviate potential warping problems after injection molding. In FIG. 4, the water inlet 407 and air inlet 405 are shown connecting with the cavity 409 formed by vertical ribs as shown in FIG. 4a.

In FIG. 5 is shown an embodiment containing a separate threaded cap 503 which is free to rotate without rotating body 501 and contains internal threads 505. The outlet fittings, inlet fittings, and other elements are substantially the same as in the other figures.

Other adaptations of the subject invention are shown in FIG. 6. Shown at 601 and 603 are durable (non-disposable) adapters which alter the fluid paths of the turbine air and cooling air and water. In a preferred embodiment, the turbine air supply and turbine air return are directed to paths around the internal periphery of the device 605, either as separate concentric paths or as paths which divide to each share a separate half of the device. The cooling water supply is directed into a central pathway which is filtered by a disk filter while the cooling air supply is concentric with the cooling water and is filtered by a washer shaped filter. A device suitable for filtering the cooling air and water is illustrated in FIG. 7. The housing of the device will be modified to provide for the large volume air passages which will be routed around the periphery of the device.

Referring now to FIG. 7, an exploded view of the filter/ syringe device illustrates the water inlet tube 701 and surrounding polymer sleeve connector 703 containing concentric air passages 704 and O-ring groove 705, as shown in FIG. 1b. Inlet housing 707 is preferably molded integral with connector 704, and has a portion of reduced diameter 709 on the outlet side, forming a shoulder 711 used to seal the device, preferably by solvent bonding, but optionally using other techniques such as ultrasonic welding. Connecting sleeve 703 extends inward of the inlet housing at 712, the sleeve at this point having radially extending passages through which air may flow from concentric passages 704 into the air filtration chamber which is formed upon assembly.

The washer-shaped air filtration microporous membrane is shown at 713. Upon assembly it is solvent-bonded or thermal-bonded to raised annular steps on the inlet side of grid 715. Grid 715 preferably has radially extending slots in the face abutting air filtration membrane 713 such that grid 715 provides both support for membrane 713 against the air pressure impinging upon it as well as providing for high flow passages for air. The radially extending slots terminate at a radially concentric groove which is pierced with holes to allow filtered air to pass by grid 715. Grid 715 has a central opening 717 through which water inlet tube 701 passes.

At 719 is the water filtration microporous membrane, having a diameter less than that of the aforementioned radially extending groove, and sealed against a concentric raised portion of disk 715. The water filtration membrane is supported against impinging water pressure by the inlet face of outlet housing 721, which, like disk 715, has radially extending slots on the inlet side facing water filtration membrane 719 to allow full fluid flow. Unlike disk 715, where air flow is toward the circumference of the device, water flow is toward the central axis. Syringe tip 723 is advantageously molded onto outlet housing 721 and is structured as in the connecting sleeve on inlet housing 707. Water outlet tube 725 is inserted into syringe tip 723, or the outlet housing and syringe tip may be molded around the water outlet tube. Following assembly, the combined air/ water syringe may be bent to the angle desired for use.

FIG. 8 illustrates one embodiment of the central grid 815 to which the air filtration microporous membrane is sealed. The device is disk-shaped with several radially concentric shoulders. Shoulder 801 is a sealing shoulder against which the corresponding sealing surface of the inlet housing will be sealed, preferably by solvent bonding. Shoulder 803 is the surface onto which the outer periphery of microporous air filtration membrane will be bonded, for example by adhesive bonding, solvent bonding, thermal bonding, or ultrasonic welding. The inner periphery of the microporous membrane will be sealed to raised concentric land 805. When the device is assembled, the inner end of the inlet sleeve may abut the inner periphery of the air filtration membrane along shoulder 806 to assist in maintaining the integrity of the seal between the membrane and the disk. Radially extending slots 807 allow for air flow from the sterile side of the filter to radially concentric groove 809 which contains through slots or holes 811 to allow air to flow through the disk. The disk further contains axial through passage 813 through which the water inlet tube passes, and to which the disk is sealed.

Figure 9:
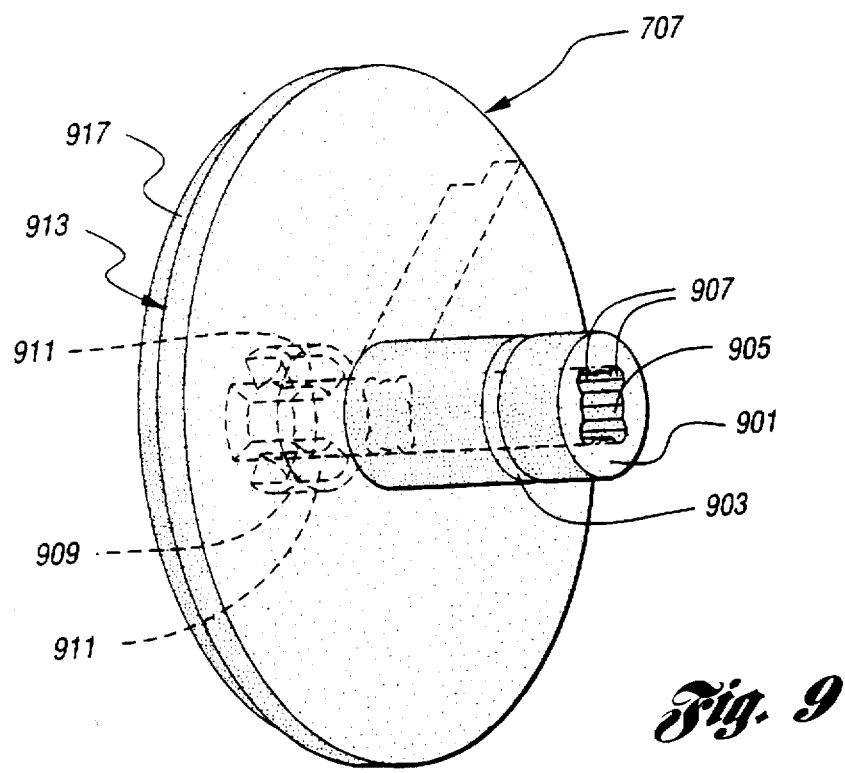
FIG. 9 is an inlet housing as depicted in FIG. 7.

Referring to FIG. 9, the inlet housing 707 is shown without the water inlet tube, which may be inserted and bonded to the inlet sleeve or around which the inlet sleeve may be injection molded. The cylindrical connective sleeve 901 extends away from the face of the inlet housing and is dimensioned to slide into the mating bore in the syringe handset. At 903 is the annular groove adapted to receive the sealing O-ring located in the bore of the handset. Inlet bore 905 is dimensioned to receive the outer diameter of water inlet tube 701, and additionally has recesses 907 to receive air flow. On the reverse side (outlet side) of inlet housing 707 is a corresponding extension 909 of the sleeve, with radially extending passages 911 connecting air recess passages 907 with the air chamber which is formed upon assembly.

On the outlet side of the device is a shoulder formed by a reduced radiused section. The reduced radius section 917 serves to position the inlet housing into the recess in the central grid upon assembly, the sealing face being the periphery of the disk shown at 913. Upon assembly, the innermost tip of water inlet tube 701 will pass through both the inlet housing as well as through the grid 715 to supply water to the water chamber.

The device illustrated in FIGS. 7 to 9 can be modified to provide high volume air passages by providing an additional shoulder on the device shown in FIG. 8, separated radially from the outside shoulder 1001 by a recess which is perforated with holes or slots to allow air flow, and which is connected at opposing sides by a raised rib which will contact similar raised ribs on the inlet housing, providing a path on one side of the device for turbine supply air, and on the other side a path for turbine return air. A plan view of the outermost shoulder of the support grid of FIG. 8 and the additional elements is shown as FIG. 10.

Figure 10:
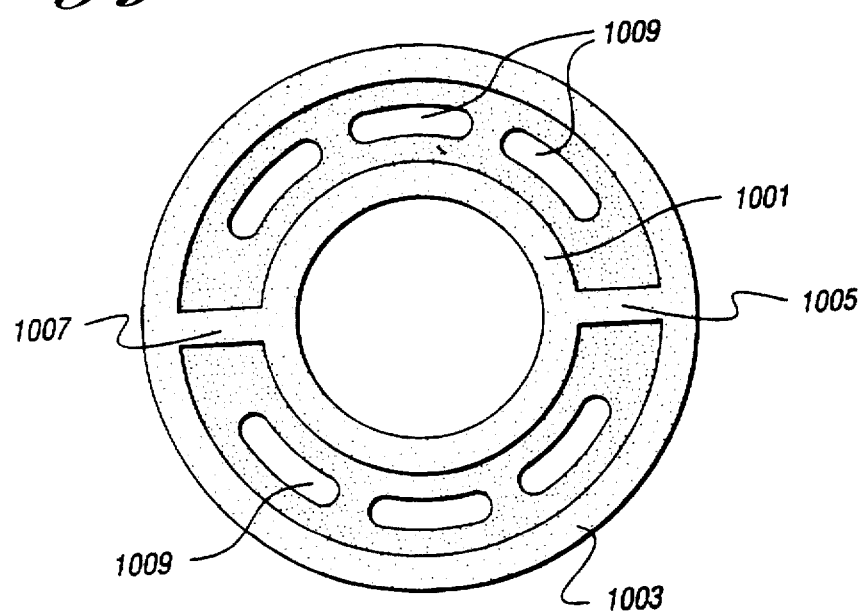
FIG. 10 depicts bilaterally symmetrical concentric turbine air and return passages in a modified support disk as depicted in FIG. 8.

In FIG. 10, at 1001 is the outside shoulder of the device of FIG. 8. Raised shoulder 1003 seals the device from the outside, against a corresponding sealing surface on the inlet housing. At 1005 and 1007 are shown raised ribs which, when sealed against corresponding raised ribs on the inlet housing, separate the turbine supply and return air paths. At 1009 are shown through slots through which air may flow.

The advantage of the device of FIGS. 7 through 10 is that it may have less length and utilize manufacturing techniques common to other filters, lowering the cost. The inlet housing will be provided with appropriate male fittings and external threads, while the outlet housing will be provided with an internally threaded collar and the appropriate female fittings. The arrangement of air passages, dimensioning, etc., are within the level of skill in the art.

The microporous membrane air filters may be hydrophilic or hydrophobic, preferably the latter, as otherwise condensation may affect air flow. Suitable hydrophobic filters are the VERSAPOR® microporous membranes available from GelmanSciences. The maximum pore size should be no larger than 1.0 µm. A range of 0.1 µm to 1.0 µm is preferred. To remove all microbes, a maximum pore size of approximately 0.45 µm is required. The membrane area is dependent on flow volume and period of use, but for disk filters, filter diameters of less than 30 mm, preferably less than 25 mm, and most preferably 10-20 mm are preferred. For other filter geometries, equivalent filter areas may be used. Hydrophobic PTFE filters may also be used.

The water filtration membrane must be a hydrophilic membrane or a hydrophobic membrane treated to render it hydrophilic. Suitable membranes are polyethersulfone membranes available from GelmanSciences under the trade name SUPOR® microporous membranes. The pore sizes and filter areas are in the same range as for the air filtration membranes.

The subject devices may also contain a fifth compartment or passage adapted to transmit light from a fiber optic light source located in the multilumen supply tube and a fiber optic receiving element located in the handpiece. The light passage should be straight to allow light to be transmitted without substantial reduction in intensity.

Unlike prior art devices which filter water only, and require the multilumen supply tube to be split and spliced, the filters of the subject invention are point of use devices which may easily be attached and disconnected. Moreover, the present devices completely eliminate the potential for backflow which might otherwise contaminate the supply lumens.

Having now fully described the invention, it will be apparent to one of ordinary skill in the art that many changes and modifications can be made thereto without departing from the spirit or scope of the invention as set forth herein.

What is claimed is:

1. A multicompartmental filter component suitable to filter cooling water and cooling air supplied to a turbine driven dental handpiece, comprising:

a polymeric housing having an inlet end and an outlet end, said inlet end having a turbine air supply passage, a turbine air return passage, a cooling water inlet passage, and a cooling air inlet passage;

said outlet end having a turbine air supply passage, a turbine air return passage, a cooling water outlet passage, and a cooling air outlet passage;

said housing comprising minimally four compartments;

a first compartment in communication with said turbine air supply passage in said inlet end and said turbine air supply passage in said outlet end;

a second compartment in communication with said turbine air return passage in said inlet end and said turbine air return passage in said outlet end;

a third compartment in communication with said cooling air inlet passage and said cooling air outlet passage, said third compartment containing a microporous air filtration membrane positioned such that all cooling air entering the device through said cooling air inlet passage must pass through said microporous air filtration membrane before exiting the device through said cooling air outlet passage;

a fourth compartment in communication with said cooling water inlet passage and said cooling water outlet passage, said fourth compartment containing a microporous hydrophilic water filtration membrane positioned such that all cooling water entering the device through said cooling water inlet passage must pass through said microporous hydrophilic water filtration membrane before exiting the device through said cooling water outlet passage.

2. The multicompartmental filter component of claim 1 wherein said inlet end is equipped with male fittings for each of said turbine air supply passage, turbine air return passage, cooling air inlet passage, and cooling water inlet passage, said male fittings adapted to mate with a multilumen air and water supply end fitting, and wherein said outlet;end turbine air supply passage, turbine air return passage, cooling air outlet passage, and cooling water outlet passage are adapted to mate with the respective male fittings of a dental handpiece.

3. The multicompartmental filter component of claim 2, wherein the inlet end of said component comprises a cylinder having external threads adapted to mate with internal threads of a multilumen air and water supply end fitting.

4. The multicompartmental filter component of claim 3 wherein said outlet end comprises a rotatable collar having internal threads adapted to mate with external threads of a dental handpiece.

5. The multicompartmental filter component of claim 2 further comprising a fifth compartment positioned such that light emitted by a fiber optic light source in a multilumen supply will travel unobstructed to a fiber optic receiver in said handpiece.

6. The multicompartmental filter component of claim 1 further comprising a cylindrical housing, said first through fourth compartments extending in an axial direction through said housing, said microporous air filtration membrane and said microporous water filtration membrane abutting a first side and a second side of a planar dual function filtration partition respectively, said filtration partition adapted to be sealingly mounted within said housing;

said planar filtration partition containing a filtered air chamber located within said partition communicating with the side of said microporous air filtration membrane abutting said first side of said partition, said filtered air chamber further communicating with said cooling air outlet passage in said outlet end;

said planar filtration partition containing a filtered water chamber located within said partition communicating with the side of said microporous water filtration membrane abutting said second side of said partition, said filtered water chamber communicating with said cooling water outlet passage in said outlet end.

7. The multicompartmental filter component of claim 1 further comprising a fifth compartment positioned such that light emitted by a fiber optic light source in a multilumen supply will travel unobstructed to a fiber optic receiver in said handpiece.

8. The multicompartmental filter component of claim 1 wherein said first compartment and said second compartments comprise concentric pathways surrounding a central cooling water inlet passage and a cooling air supply inlet passage.

9. The multicompartmental filter component of claim 8 wherein said first compartment and said second compartment are concentric with respect to each other.

10. The multicompartmental filter component of claim 8 wherein said first and second compartments are concentric with respect to said water inlet passage, said passages being substantially bilaterally symmetrical with respect to each other.

11. The multicompartmental filter component of claim 8 wherein said component is disk-shaped, said air filtration membrane is washer-shaped, said water filtration membrane is washer-shaped, and wherein said air filtration membrane and said water filtration membrane are plane parallel and coaxially positioned with respect to their geometric centers.

12. The multicompartmental filter component of claim 8 further comprising a fifth compartment positioned such that light emitted by a fiber optic light source in a multilumen supply will travel unobstructed to a fiber optic receiver in said handpiece.

13. The multicompartmental filter component of claim 8 wherein said air filtration membrane and said water filtration membrane are effective to remove all particulate matter having a size greater than 0.45 μm.

14. The multicompartmental filter component of claim 8 wherein said air filtration membrane and said water filtration membrane are effective to remove all particulate matter having a size greater than 0.45 μm.

15. The multicompartmental filter component of claim 1 wherein said air filtration membrane and said water filtration membrane are effective to remove all particulate matter having a size greater than 1 μm.

16. The multicompartmental filter component of claim 1 wherein said air filtration membrane and said water filtration membrane are effective to remove all particulate matter having a size greater than 0.45 μm.

* * * * *